United States Patent [19]
Maher et al.

[11] Patent Number: 6,018,208
[45] Date of Patent: Jan. 25, 2000

[54] ARTICULATED MOTOR STATOR ASSEMBLY FOR A PUMP

[75] Inventors: Timothy R. Maher, Orangevale; Douglas C. Thomas, Carmichael; Thomas C. Rintoul, Gold River, all of Calif.

[73] Assignee: Nimbus, Inc., Rancho Cordova, Calif.

[21] Appl. No.: 09/237,731

[22] Filed: Jan. 26, 1999

[51] Int. Cl.⁷ .................................................. H02K 1/12
[52] U.S. Cl. ......................... 310/254; 310/258; 310/259; 310/216; 310/217; 310/218; 310/89; 417/356; 417/423.1; 417/423.7; 415/900
[58] Field of Search ................................. 310/254, 216, 310/259, 258, 217, 218, 89; 417/356, 423, 365, 423.1, 423.7, 900, 355, 423.12, 423.15, 604, 151, 53, 206; 415/900

[56] References Cited

U.S. PATENT DOCUMENTS

| | | | |
|---|---|---|---|
| 452,717 | 5/1891 | Riker | 310/42 |
| 3,433,163 | 3/1969 | Sheets et al. | 103/87 |
| 4,625,712 | 12/1986 | Wampler | 128/1 D |
| 4,704,121 | 11/1987 | Moise | 623/3 |
| 4,806,812 | 2/1989 | Masterman | 310/182 |
| 4,846,152 | 7/1989 | Wampler et al. | 600/16 |
| 4,968,911 | 11/1990 | Denk | 310/42 |
| 4,994,078 | 2/1991 | Jarvik | 623/3 |
| 5,098,256 | 3/1992 | Smith | 415/111 |
| 5,112,200 | 5/1992 | Isaacson et al. | 417/356 |
| 5,118,264 | 6/1992 | Smith . | |
| 5,145,333 | 9/1992 | Smith | 417/405 |
| 5,158,440 | 10/1992 | Cooper et al. | 417/423.1 |
| 5,205,721 | 4/1993 | Isaacson | 417/356 |
| 5,211,546 | 5/1993 | Isaacson et al. | 417/356 |
| 5,239,221 | 8/1993 | Juan | 310/258 |
| 5,324,177 | 6/1994 | Golding et al. | 417/423.1 |
| 5,370,509 | 12/1994 | Golding et al. | 417/423.1 |
| 5,393,207 | 2/1995 | Maher et al. | 417/423.7 |
| 5,399,074 | 3/1995 | Nosé et al. | 417/423.1 |
| 5,507,629 | 4/1996 | Jarvik | 417/423.3 |
| 5,527,159 | 6/1996 | Bozeman, Jr. et al. | 417/45 |
| 5,588,812 | 12/1996 | Taylor et al. | 417/356 |
| 5,707,218 | 1/1998 | Maher et al. | 417/356 |

Primary Examiner—Nestor Ramirez
Assistant Examiner—Saeed Ghahramani
Attorney, Agent, or Firm—Fish & Richardson P.C., P.A.

[57] ABSTRACT

An articulating motor stator assembly for use in a pump incorporates features that permit recycling of the motor stator when disposing of other parts of the pump. Such a stator assembly facilitates convenient manufacture, testing, and installation of the pump. For convenient installation, the motor stator assembly can incorporate a multi-part, annular housing that defines a central conduit to receive a motor rotor assembly. The multi-part housing of the motor stator assembly may be selectively repositioned between an open and closed configuration. In its open configuration a motor rotor assembly may be conveniently installed in the motor stator and when closed the motor stator will actuate the motor rotor assembly in order to operate a pump. The assembly thereby enables separate manufacture and shipment from a remote location. In addition, the assembly can be separately tested prior to installation. After pump use, the motor stator can be opened so as to remove the motor rotor assembly. The same motor stator assembly can then receive a new motor rotor assembly.

28 Claims, 5 Drawing Sheets

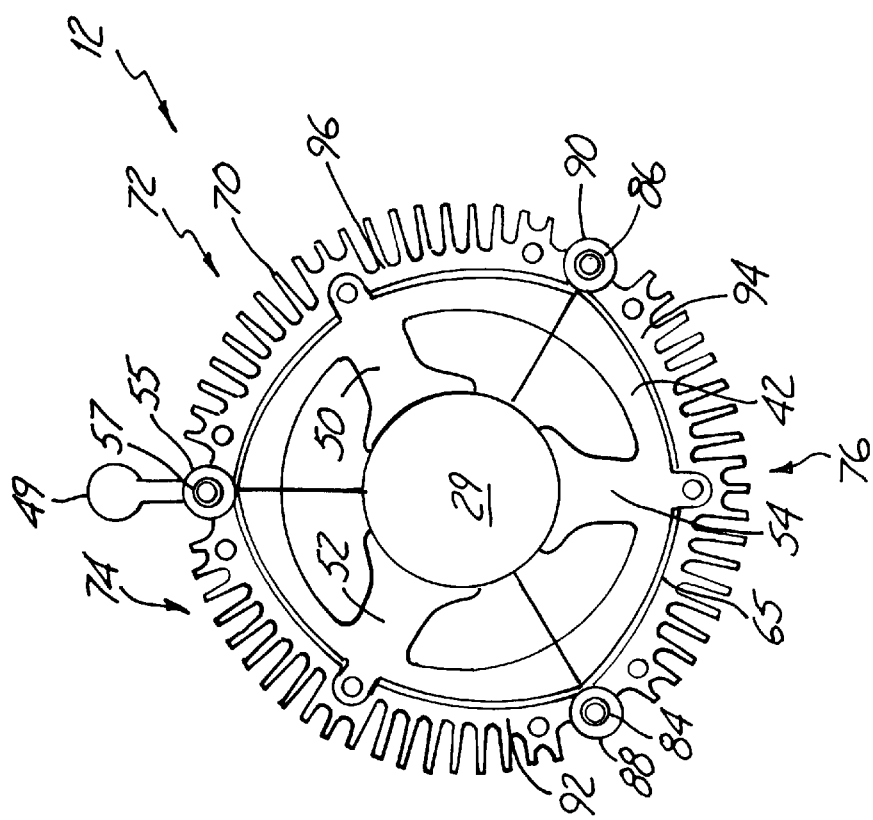
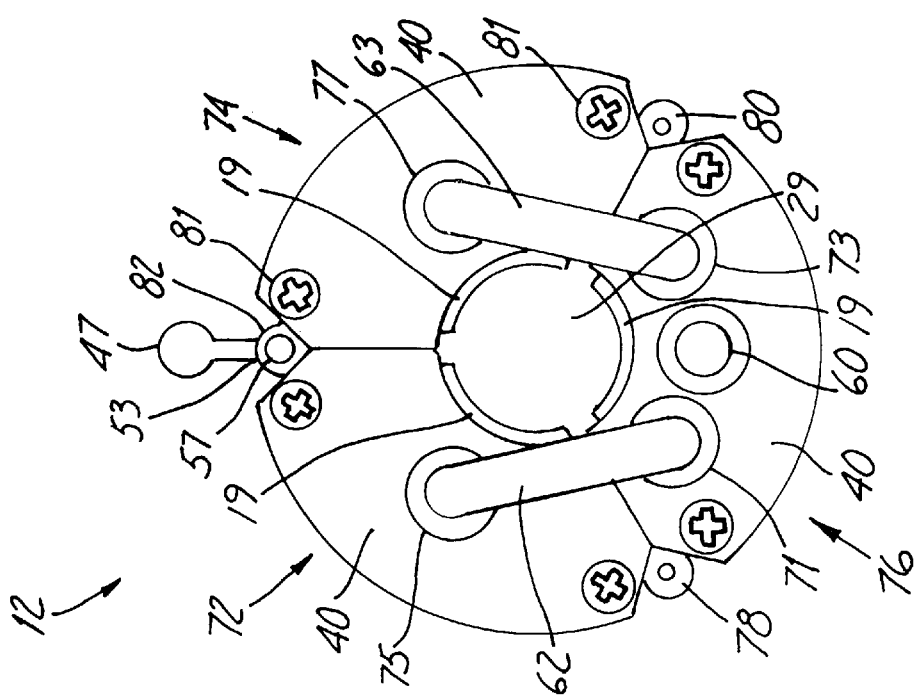

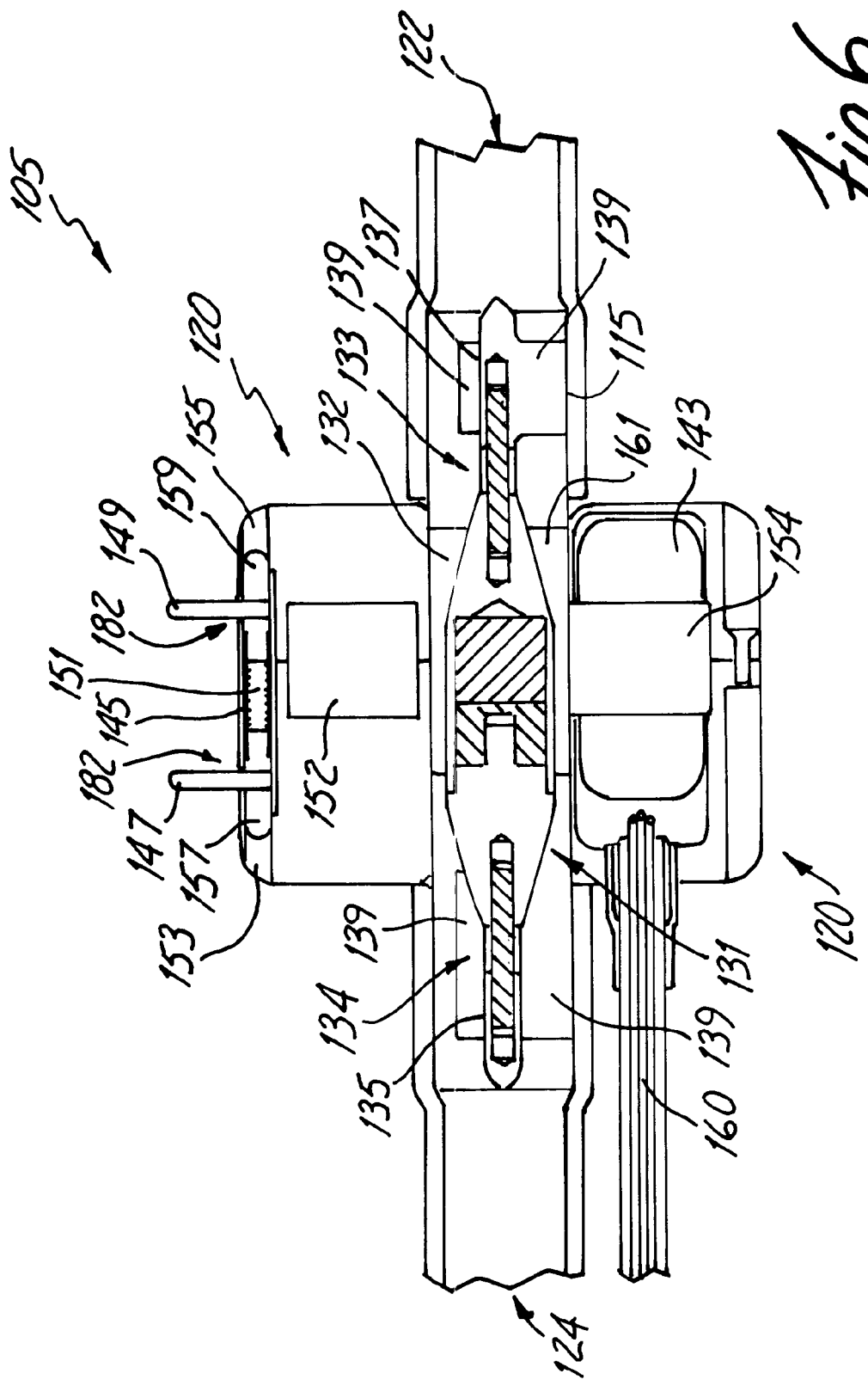

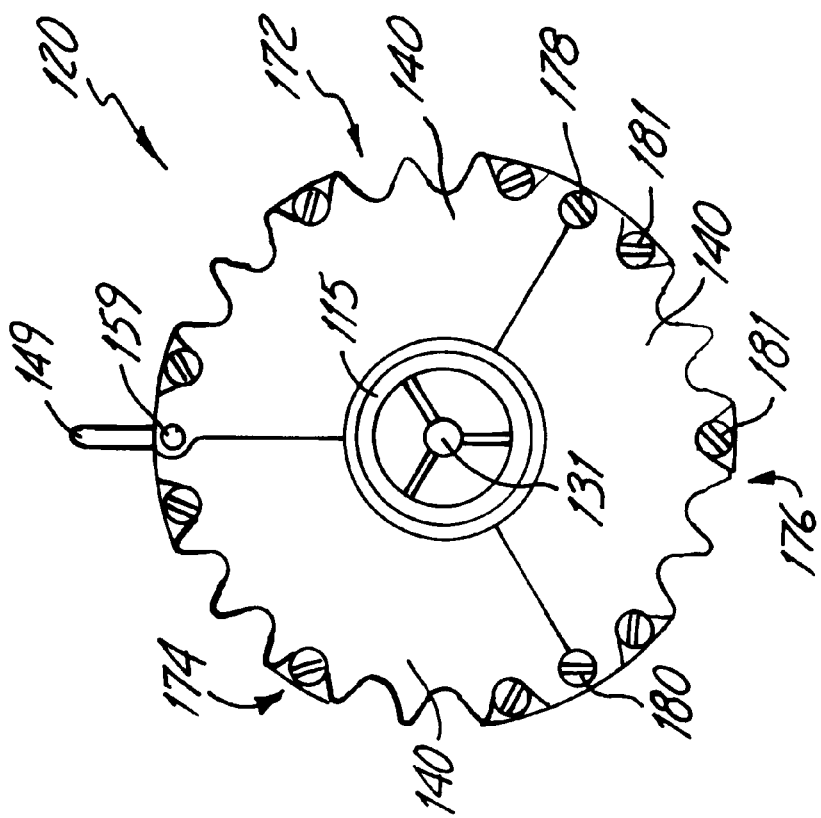
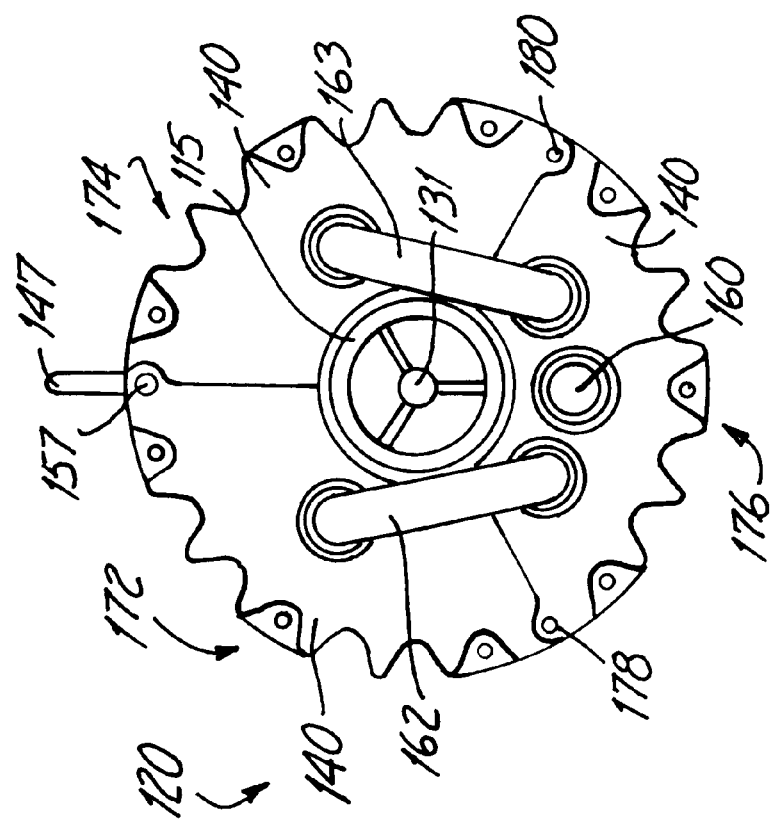

ARTICULATED MOTOR STATOR ASSEMBLY FOR A PUMP

TECHNICAL FIELD

The present invention relates to electric motor assemblies and, more particularly, to pump motor stator assemblies that may be useful, e.g., in blood pump applications.

BACKGROUND INFORMATION

A number of implantable blood pumps presently are under development for application as either artificial hearts or cardiac assist devices. Both centrifugal and axial-flow pumps can be utilized in blood pumps.

A typical blood pump includes a pump housing that defines an inflow port, an outflow port, a pumping chamber, an impeller mechanism mounted within the pumping chamber, an electric motor rotor coupled to the impeller mechanism for blood pumping action, and an electric motor stator that actuates the rotor by an electromagnetic force. The impeller mechanism can be mechanically coupled to the rotor via a transmission shaft as in, for example, a centrifugal-flow type pump. Alternatively, the impeller mechanism or blades can be attached directly to the rotor as in, for example, an axial-flow pump.

The motor stator typically includes three or more groups of windings. Each winding group is formed from a conductive wire wound around a stack of metallic stampings. The motor rotor contains a permanent magnet. In effect, the stator and rotor together form a brushless dc motor. Typically, the windings are disposed around the rotor. Thus, the stator is annular in shape, forming a ring-like structure that extends around the rotor. In operation, the stator windings are sequentially energized, which creates a rotating magnetic field that drives the rotor about its longitudinal axis. In some cases, the annular stator is positioned in the wall of the pump housing, around the rotor. In axial-flow pump designs, the stator is mounted about the blood flow conduit. In centrifugal-flow pumps, the stator is mounted about a rotor neck that is connected to an impeller mechanism located within the blood flow.

In view of an application of a blood pump in artificial hearts and/or cardiac assist devices, reliability is a critical performance factor. Moreover, blood pumps must ensure that a patient's blood does not become contaminated during use of the pump by blood contacting pump parts that are outside of the blood conduit. As such, pump components are machined to exacting specifications to minimize pump failure and ensure the integrity of the blood pathway. Consequently, pump components are often very expensive. Accordingly, design improvements that can decrease overall consumer cost remain a constant focus of blood pump development.

SUMMARY

The present invention is directed to an articulating motor stator and a pump incorporating such a stator. The articulating motor stator is particularly useful for blood pumps, but may find ready application in other rotary pump applications, including both centrifugal and axial flow arrangements.

Blood pumps are often used on human patients for short time periods, during surgery or other medical procedures, or while the patient is in, or recovering from, a critical condition. Even though after use a pump may remain in perfect working condition, the entire pump is often discarded rather than being reused. Such pump disposal protects against exposing a subsequent patient to infection or other bio-incompatibilities contained within a usual pump. Nevertheless, it is desirable to recycle and re-sterilize the expensive components of a blood pump, e.g. the stator, between patients or when other parts of the pump require replacement.

An articulated or hinged motor stator allows convenient installation and removal of the stator relative to a blood flow conduit containing a rotor element and an associated impeller mechanism. In this manner, the stator can be readily removed from a pump for repair, maintenance, replacement, or reuse. In particular, the articulating motor stator can be reused in multiple pumps. An articulated motor stator in accordance with an embodiment of the present invention is useful for blood pumping applications and, more particularly, can be used in an extracorporeal blood pump.

Often, blood pump seals fail at a higher frequency than other pump components. When such a failure occurs, the entire blood pump is replaced so as to prevent contaminating a patient's blood stream. An articulated motor stator in accordance with the present invention provides a cost effective alternative to replacing an entire pump when only a portion of the pump has failed. This advantage is significant because the motor stator cost is a significant portion of the total cost of a blood pump. Additionally, a removable articulating stator placed outside a patient's sterile field can be immediately re-used or replaced without requiring a cleaning or sterilization step.

A motor stator assembly constructed according to the present invention allows the stator assembly to be opened, the motor rotor removed and replaced, and the original stator assembly to be quickly re-assembled and reused. Such a motor stator assembly is substantially annular in shape and is constructed of two or more sub-assemblies, defining distinct azimuthal parts of the motor stator assembly. The sub-assemblies can be mechanically connected via hinges, allowing opening and closing of the motor stator assembly in a clamshell-like manner. The stator windings are electrically connected to electrically conductive terminals mounted within the housing via flexible interconnections, so that electrical continuity between the windings and terminals is unaffected by opening and closing the stator.

A motor stator assembly constructed according to the present invention also enables convenient manufacture, testing, and installation without significant risk of stator damage. In particular, the motor stator assembly may form a discrete component that may be added to, or removed from, the blood pump with ease, enabling separate manufacture and shipment from a remote location. In addition, several motor rotor assemblies may be easily tested with one motor stator assembly of the present invention in order to optimize the match between the two components of the motor. Furthermore, the motor rotor assembly and blood conduit may be connected to blood vessels in a sterile environment, followed by installation of the motor stator assembly about the blood conduit.

In one embodiment, the present invention provides a motor stator assembly for use in a blood pump, the motor stator assembly defining a central aperture configured to receive a motor rotor assembly wherein the motor stator includes stator windings and a housing enclosing the motor stator wherein the housing contains two or more sub-assemblies that are selectively repositionable to allow installation and removal of the motor stator relative to the rotor assembly.

In another embodiment, the present invention provides a motor stator assembly for use in a blood pump, the motor stator assembly defining a central aperture configured to receive a motor rotor assembly, a motor stator that includes stator windings, and a housing enclosing the motor stator, wherein the housing contains two or more sub-assemblies that are selectively repositionable to allow installation and removal of the motor stator relative to the motor rotor assembly, and wherein the sub-assemblies are mechanically joined by, and pivotable about, hinge members to define an open configuration in which the sub-assemblies extend away from each other, and a closed configuration in which the sub-assemblies extend towards each other to define a substantially annular aperture for receipt of the motor rotor assembly.

In a further embodiment, the present invention provides a motor stator assembly for use in a blood pump, the motor stator assembly containing a central aperture configured to receive a motor rotor assembly, a motor stator that includes stator windings and that is substantially annular in shape, thereby defining a ring-like portion and a conduit, and wherein the assembly includes a plurality of sub-assemblies, each subassembly forming an azimuthal portion of the assembly and containing an azimuthal portion of the motor stator.

In another embodiment, the present invention provides a motor stator assembly for use in a blood pump containing a central aperture configured to receive a motor rotor assembly, a motor stator, being substantially annular in shape and thereby defining a ring-like portion and a conduit, wherein the motor stator includes stator windings, and wherein the assembly contains a plurality of sub-assemblies, wherein each sub-assembly forms an azimuthal portion of the assembly and contains an azimuthal portion of the motor stator, and wherein one or more sub-assemblies are mechanically joined by, and pivotable about, hinge members, to define an open configuration in which the sub-assemblies extend away from each other, and a closed configuration in which the sub-assemblies extend towards each other to define a substantially annular aperture for receipt of the motor rotor assembly.

In a further embodiment, the present invention provides a blood pump containing a central aperture configured to receive a motor rotor assembly, a motor stator, wherein the motor stator is substantially annular in shape and thereby defines a ring-like portion and a conduit, and wherein the motor stator includes stator windings, a motor stator assembly containing a plurality of sub-assemblies, wherein each distinct assembly forms an azimuthal portion of the motor stator assembly and contains an azimuthal portion of the motor stator, and wherein one or more sub-assemblies are mechanically joined by, and pivotable about, hinge members, to define an open configuration in which the sub-assemblies extend away from each other, and a closed configuration in which the subassemblies extend towards each other to define a substantially annular aperture for receipt of a motor rotor assembly, and a motor rotor that fits within the motor stator assembly, the motor rotor assembly being so positioned within the motor stator assembly as to cooperate with the motor stator assembly to form an electric motor when positioned within the motor stator assembly.

In a further embodiment, the present invention provides a method of assembling a blood pump, the blood pump containing a motor stator assembly, including a central aperture configured to receive a motor rotor assembly, wherein the motor stator assembly is substantially annular in shape and thereby defines a ring-like portion and a conduit, and wherein the motor stator assembly includes stator windings, and wherein the motor stator assembly contains a plurality of sub-assemblies, each sub-assembly including a portion of the motor stator, by selectively positioning the sub-assemblies in an open configuration to install the motor rotor assembly within the motor stator assembly and selectively repositioning the sub-assemblies in a closed configuration so that the motor stator assembly fits snugly around the motor rotor assembly.

In another embodiment, the present invention provides a method of connecting a blood pump to a living being, the blood pump containing a motor rotor assembly including a blood flow conduit, a motor stator assembly including a central aperture configured to receive the motor rotor assembly, wherein the motor stator assembly is substantially annular in shape and thereby defines a ring-like portion and a conduit, and wherein the motor stator assembly includes stator windings, and wherein the motor stator assembly contains a plurality of sub-assemblies, each sub-assembly including a portion of the motor stator, and wherein the blood flow conduit of the motor rotor assembly is attached to the blood vessels of the living being, and wherein the sub-assemblies are selectively positioned in an open configuration to install the motor stator assembly about the motor rotor assembly connected to the living being, and wherein the motor stator's sub-assemblies are selectively repositioned in a closed configuration so that the motor stator assembly fits snugly around the motor rotor assembly.

DESCRIPTION OF DRAWINGS

FIG. 2 is an end view, depicting the motor stator assembly of FIG. 1;

FIG. 3 is another end view, depicting the motor stator assembly of FIG. 1;

FIG. 6 is a longitudinal cross-sectional side view diagram depicting an axial-flow blood pump incorporating an articulating motor stator;

FIG. 7 is an end view of the motor stator assembly of FIG. 6; and

FIG. 8 is another end view of the motor stator assembly of FIG. 6.

Like reference numbers and designations in the various drawings indicate like elements.

DETAILED DESCRIPTION

Figure 1:
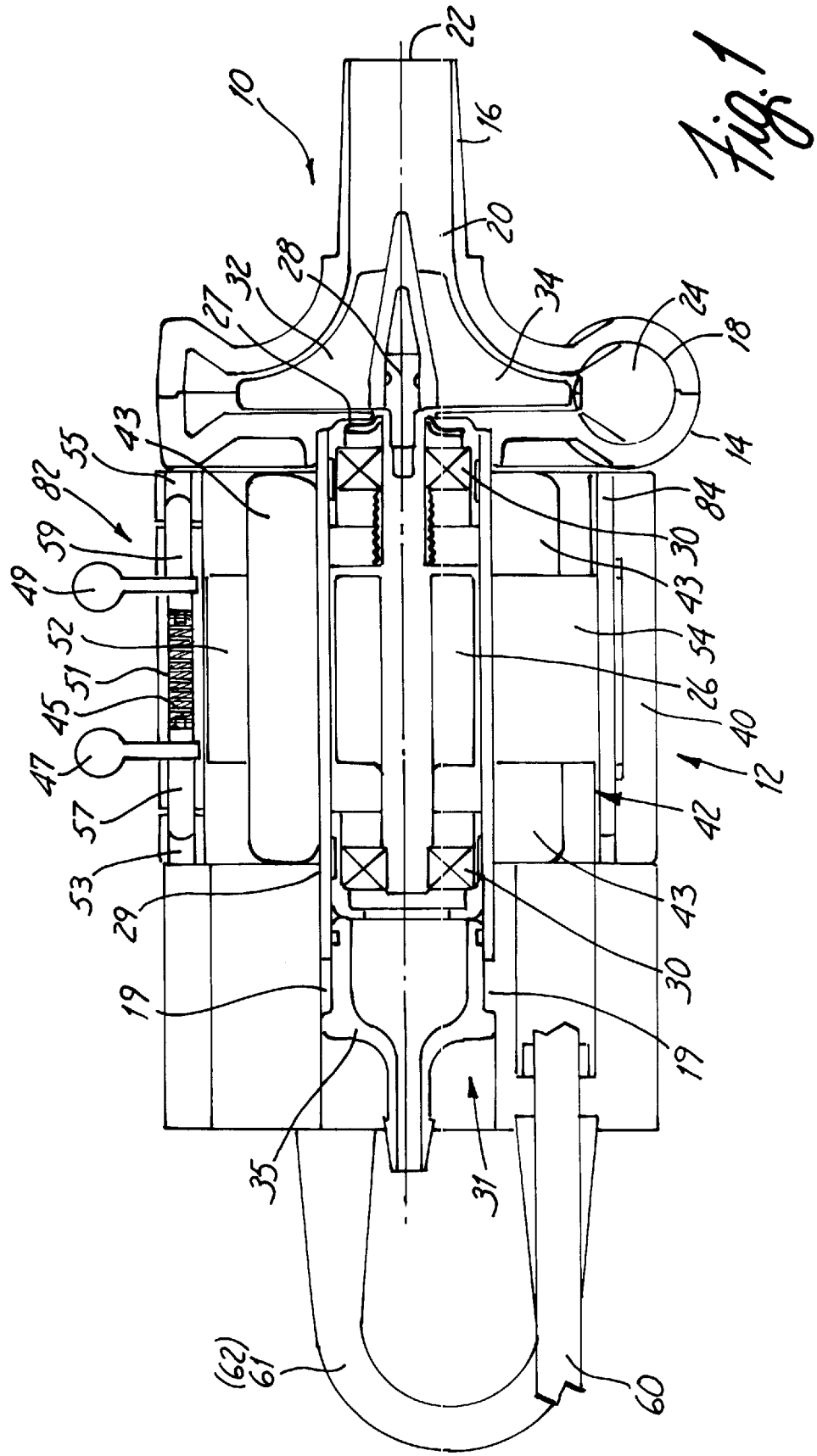
FIG. 1 is a longitudinal cross-sectional diagram depicting a centrifugal-flow blood pump incorporating an articulating motor stator incorporating aspects of the invention.

FIG. 1 is a longitudinal cross-sectional diagram of a centrifugal-flow blood pump 10 incorporating an articulating stator motor assembly 12 in accordance with an embodiment of the present invention. Pump 10 can be connected to an animal, e.g. a human, to function as an artificial heart or a cardiac assist device. As shown in FIG. 1, pump 10 includes a housing 14 having an inflow portion 16 and an outflow portion 18. Inflow portion 16 has an inflow opening 22 through which blood enters blood pumping chamber 20. Outflow portion 18 has an outflow opening 24 through which blood exits pumping chamber 20. Inflow and outflow portions, 16, 18 can be fitted with additional hardware (not shown) designed to be joined with the cardiovascular system for operation. Rotor 26 is mounted within bearing blocks 30 and coupled to transmission shaft 28. Impeller blades 32, 34 are mounted on transmission shaft 28 and oriented to impart centrifugal pumping energy to the blood flow upon actuation of the rotor. A seal 27 can be provided about transmission shaft 28 between rotor 26 and impeller blades 32, 34. In FIG. 1, only two impeller blades 32, 34 are visible. However, transmission shaft 28 may carry three or more impeller blades, each arranged, for example, in a fan-like pattern. Housing 14 and the other components of pump 10 can be fabricated from bio-compatible materials.

Motor stator assembly 12 is generally annular in shape, defining a central conduit 29 for receiving the motor rotor assembly 31. Motor rotor assembly 31 is held in place by locating piece 35, which is seated on flanges 19. With further reference to FIG. 1, motor stator assembly 12 includes a stator housing 40 that encloses a motor stator 42. Motor stator 42 has three or more separate groups of electrical windings 43 that surround metal stampings 52, 54. An electrical conduit 60 is coupled to the motor stator assembly 12. Electrical conduit 60 carries electrical cables to motor stator assembly 12 for connection to the electrical windings 43 of metal stampings 54. Electric current is supplied to additional winding groups 43 via flexible cable connections 62, 63 (63 not shown in FIG. 1).

FIG. 2 is an end view of the motor stator assembly 12 illustrating the electrical connections of subassemblies 72, 74, 76 that when together define a substantially annular central conduit 29. Current is supplied to the motor stator assembly 12 via electrical conduit 60. Subassemblies 72, 74, 76 are supplied electrical current via flexible interconnectors 62, 63. Three phase current can be applied to motor stator assembly 12. In such an arrangement, each subassembly 72, 74, 76 would receive one phase. As such, each subassembly 72, 74, 76 would have one hot and one return wire coupled to its windings. In the exemplary embodiment of FIG. 2, all of the leads enter motor stator assembly 12 via electrical conduit 60 in subassembly 76. Individual leads and returns are routed from subassembly 76 to subassemblies 72, 74 via flexible interconnectors 62, 63.

Also visible in FIG. 2 are the stator housings 40 that cover each of subassemblies 72, 74, 76. Each stator housing 40 can be attached to stator 42 (not pictured) by any conventional manner. For example, in FIG. 2, housing 40 is attached to a stator by screws 81. Each of subassemblies 72, 74, 76 can be filled with an insulating or damping material, if desired, to electrically and mechanically isolate the stator windings from housing 40. Subassemblies 72, 74, 76 are connected via hinges 78, 80 and a detent locking mechanism 82, which incorporates tab 47 (explained in detail below). Stator housing 40 can be of alternative designs. For example, stator housing 40 can be designed to extend across the entire, part, or none of the motor stator. As depicted in FIG. 1, stator housing 40 extends the entire length of the motor stator 42. Furthermore, although the motor stator assembly 20 of FIGS. 1–5 contains three subassemblies, it is to be understood that the motor stator assembly 20 can be constructed from two or more subassemblies.

FIG. 3 is conceptual end view of motor stator assembly 12 viewed from the pump 10 side. Pump 10 and motor stator housings 40 are shown as being removed in FIG. 3 to facilitate the view of motor stator assembly 12. As shown in FIG. 3, subassemblies 72, 74, 76 of motor stator 42 surround the central conduit 29 wherein the motor rotor assembly 31 (not shown) is placed during operation. Motor stator 42 has three or more stacks of metal stampings 50, 52, 54 surrounded by a ring-like portion 65. Metal stampings 50, 52, 54 are wrapped by wire windings 43 (not pictured) that occupy the winding space 56. Attached to the ringlike portion 65 are multiple cooling fins 70 designed to dissipate heat generated by the motor stator 42.

With further reference to FIGS. 2 and 3, motor stator sub-assemblies 72, 74, 76 can be mechanically connected to each other via hinges 78, 80 and detent locking mechanism 82. Hinges 78 and 80 comprise hollow cylinders 88, 90, and cylindrical pivot pins 84, 86 whose outer diameter is nearly equal to the inner diameter of hollow cylinders 88, 90. Hinges 78, 80 provide pivot points about which the subassemblies 72, 74, 76 rotate when the detent locking mechanism 82 is opened. It is to be understood that stator subassemblies 72, 74, 76 in accordance with the present invention may be coupled via an acceptable manner that enables the subassemblies to articulate about a pivot point. Together, the stator subassemblies 72, 74, 76 articulate to a point such that a motor rotor can be radially extracted from or inserted in central conduit 29 when the stator subassemblies are in an opened configuration.

Figure 5:
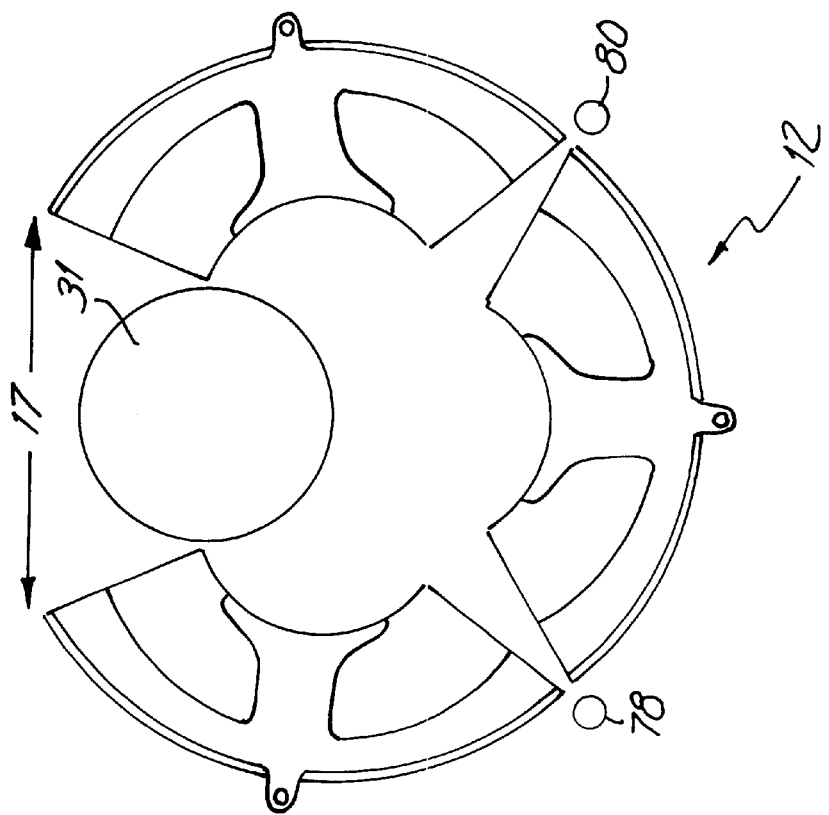
FIG. 5 is a conceptual cross-sectional end view of the motor stator assembly of FIG. 1 in an open position.
Figure 4:
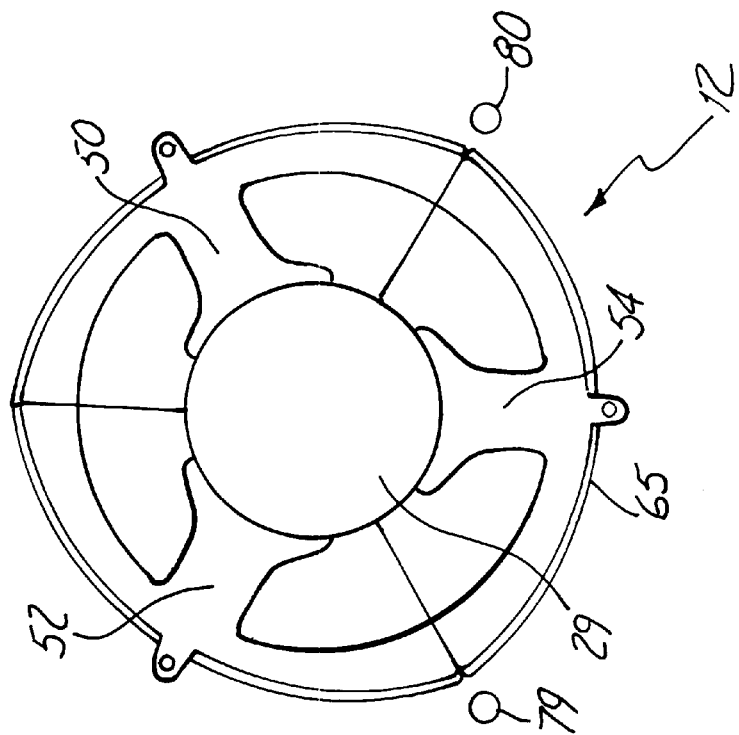
FIG. 4 is a conceptual cross-sectional end view of the motor stator assembly of FIG. 1 in a closed position.

FIGS. 4 and 5 conceptually depict the closed and open configuration of the motor assembly 12, respectively. Briefly, when motor stator assembly 12 is in its closed position the motor rotor assembly 31 (not pictured) occupies the central conduit 29 and fits somewhat snugly within metal stampings 50, 52, 54. Motor rotor assembly 31 can be separated from the inner walls of conduit 29 and motor stator assembly 12 by a tube, if desired. For a centrifugal application in which the rotor assembly 31 is not in contact with the pumping fluid, separation may not be necessary. For axial flow arrangements, however, an additional tube ordinarily will be used. As is apparent from FIGS. 4 and 5, the distance between the subassemblies 72, 74, 76 will change when the motor stator 12 is opened. Thus, the flexible cable interconnections 62, 63 (not pictured) should be sufficiently long and flexible to allow the opening of the motor stator 12 without damaging the electrical connections. This can be achieved by manufacturing methods known to those of skill in the art. When motor stator sub-assemblies 72, 74, 76 are in their open position, as in FIG. 5, an azimuthal gap 17 exists between two of the sub-assemblies. Azimuthal gap 17 should be large enough to allow motor rotor assembly 31 to be radially extracted from motor stator assembly 12.

With reference to FIGS. 1–5, motor stator 12 is opened and closed using a detent locking mechanism 82. Returning to FIG. 1, the detent locking mechanism 82 contains two tabs 47, 49 that are connected to sliding pins 57, 59. Sliding pins 57, 59 travel within, and along the axis of a cylindrical channel 51, which is coupled to subassembly 72. Sliding pins 57, 59 are held apart by a spring 45 that is disposed within the cylindrical channel 51 and is seated between sliding pins 57, 59. When spring 45 is in its relaxed position, sliding pins 57, 59 are forced apart and slide into capture channels 53, 55. Capture channels 53, 55 are located on the adjoining motor stator sub-assembly 74 such that when spring 45 is in its relaxed position, forcing sliding pins 57, 59 into capture channels 53, 55, motor stator sub-assemblies 72, 74 are locked together and the motor stator assembly is in its closed position, as shown in FIG. 4. When tabs 47, 49 are forced together, e.g., by a human thumb and forefinger, along an axis approximately parallel to an axis defined by cylindrical channel 51, spring 45 is compressed and sliding pins 57, 59 are withdrawn from capture channels 53, 55. When sliding pins 57, 59 are withdrawn from capture channels 53, 55, motor stator sub-assemblies 72, 74 are not locked together. When motor stator sub-assemblies 72, 74 are unlocked, the subassemblies 72, 74, 76 are free to rotate about hinges 78, 80 as shown in FIG. 5, which facilitates radial insertion or extraction of the motor rotor assembly 31.

After motor rotor assembly 31 is inserted into motor stator assembly 12, motor stator assembly 12 may be returned to its closed configuration, as seen in FIG. 4, by pivoting motor stator sub-assemblies 72, 74, 76 about hinges 78, 80 and locking detent mechanism 82 to join motor stator sub-assemblies 72, 74. When the motor stator assembly 12 is closed, the motor rotor assembly 31 seats on flanges 19 via locating piece 35 as seen in FIG. 1. With motor rotor assembly 31 locked within motor stator assembly 12, the motor can operate blood pump 10.

With further reference to FIGS. 1–3, current is carried to motor stator 42 via electrical conduit 60. Inside of motor stator assembly 12, winding group 43, wound around metal stamping stack 54, is energized via electrical connections contained entirely within motor stator sub-assembly 76. Winding groups (not shown) wound around metal stampings 50, 52, in motor stator sub-assemblies 72, 74 are energized via flexible cable connections 62, 63 that run between motor stator sub-assemblies 76, 72 and 76, 74, respectively. Flexible cable connections 62, 63 are connected to motor stator sub-assemblies 76, 72 and 76, 74 at electrical receptacles 71, 75 and 73, 77, respectively. Because the distance between electrical receptacles 71, 75 and 73, 77 changes as motor stator assembly 12 is moved between its open (FIG. 5) and closed (FIG. 4) positions, electrical connections 62, 63 between motor stator sub-assemblies, 72, 74, 76 preferably are flexible so that electrical current flows to windings 43 when motor stator assembly is opened and returned to its closed position (FIG. 4).

In another embodiment, axial-flow blood pumps can be adapted to incorporate an articulating motor stator assembly. FIG. 6 depicts a longitudinal cross-sectional diagram of an axial-flow blood pump 105 incorporating the invention. Motor stator assembly 120 is held in its closed configuration by a detent locking mechanism 182 that consists of tabs 147, 149 and sliding pins 157, 159. Sliding pins 157, 159 travel within, and along the axis of a cylindrical channel 151, which is coupled to subassembly 172. Sliding pins 157, 159 are held apart by a spring 145 that is disposed within the cylindrical channel 151 and is seated between sliding pins 157, 159. When spring 145 is in its relaxed position, sliding pins 157, 159 are forced apart and slide into capture channels 153, 155. Capture channels 153, 155 are located on the adjoining motor stator sub-assembly 174 such that when spring 145 is in its relaxed position, forcing sliding pins 157, 159 into capture channels 153, 155, motor stator sub-assemblies 172, 174 are locked together and the motor stator assembly is in its closed position, as shown in FIG. 6. When tabs 147, 149 are forced together, e.g. by a human thumb and forefinger, along an axis approximately parallel to an axis defined by cylindrical channel 151, spring 145 is compressed and sliding pins 157, 159 are withdrawn from capture channels 153, 155. When sliding pins 157, 159 are withdrawn from capture channels 153, 155, motor stator sub-assemblies 172, 174 are unlocked and the subassemblies 172, 174, 176 are free to rotate about hinges 178, 180 shown in FIG. 7.

In its closed configuration, motor stator assembly 120 defines a substantially annular passage surrounding a blood flow conduit 115. Blood is physically pumped by a motor rotor assembly 131 contained within the blood flow conduit 115. The motor rotor assembly 131 is disposed between two ball-and-cup bearings 133, 134 that are proximal to a blood inflow passageway 122 and proximal to a blood outflow passageway 124, respectively. Ball-and-cup bearings 133, 134 can be realized by providing one end of rotor assembly 131 with substantially spherical convex shape for engagement with a bearing block 137 having a substantially spherically concave shape, while providing the other end of rotor assembly 131 with a substantially spherical concave shape for engagement with a bearing block 135 having a substantially spherically convex shape. Bearing blocks 135, 137 can be supported within conduit 115 by flow stator blades 139 that extend radially outward from the blocks and contact with an inner wall of the conduit.

Pumping is achieved by impeller blades 132, 161 that are attached to the motor rotor assembly 131 which in turn is actuated by the motor stator assembly 120. Motor rotor assembly 131 carries one or more magnets for interaction with motor stator assembly 120. FIG. 6 depicts only two impeller blades. It is to be understood, however, that the motor rotor assembly 131 can provide one or more impeller blades. Motor stator assembly 120 actuates the motor rotor assembly 131 via an electromotive force created when electric current is supplied to wire windings 143 surrounding metal stampings 150 (not pictured), 152, 154 via electric conduit 160.

FIG. 7 and FIG. 8 are conceptual end views of a motor stator assembly 120 as shown in FIG. 6. The articulating motor stator assembly 120 is substantially the same as that for the motor stator assembly 20. Briefly, motor stator assembly 120 includes subassemblies 172, 174, 176. Sub-assemblies 172, 174, 176 contain metal stampings 150, 152, 154 (not pictured) that are enclosed in motor stator housings 140. The subassemblies 172, 174, 176 are held together via hinges 178, 180 and tabs 147, 149 in combination with sliding pins 157, 159. Referring to FIGS. 7 and 8, unlike a centrifugal-flow pump, the blood flow conduit 115 passes through the entire length of the motor stator assembly 120. Thus, blood flow conduit 115 forms a tube that is inserted within the central aperture defined by motor stator assembly 120. Contained within the blood flow conduit 115 is the motor rotor assembly 131. Motor stator housings 140 can be coupled via any acceptable method including, e.g., screws 181 as depicted in FIG. 8. Electrical connections between subassemblies 172, 174, 176 are achieved using flexible electrical interconnectors 162, 163. The flexible electrical interconnectors are of sufficient length and flexibility to facilitate removal of the motor stator assembly 120 from the blood flow conduit 115 similar to that depicted in FIGS. 4 and 5.

Other design features of an articulated motor stator assembly in accordance with the invention can be modified as necessary to accommodate the physical characteristics of alternative motor rotor assembly designs including known differences between axial-flow and centrifugal-flow pumps. Also, in addition to blood pumps, an articulated stator assembly can be adapted for other pumping applications.

The foregoing detailed description has been provided for a better understanding of the invention and is for exemplary purposes only. Other aspects, advantages, and modifications are within the scope of the following claims.

What is claimed is:

1. A motor stator assembly for use in a blood pump, the motor stator assembly defining a central aperture configured to receive a motor rotor assembly, the stator assembly comprising:

a motor stator, wherein the motor stator includes stator windings; and a housing enclosing the motor stator, wherein the housing and stator together form two or more sub-assemblies, the sub-assemblies each comprising a portion of the stator, including a respective stator winding, and a portion of the housing, the sub-assemblies being selectively repositionable to allow installation and removal of the motor stator assembly relative to the motor rotor assembly while the sub-assemblies remain mechanically interconnected.

2. The motor stator assembly of claim 1, wherein the sub-assemblies are mechanically joined by, and pivotable about, hinge members to define an open configuration in which the sub-assemblies are pivoted away from each other, and a closed configuration in which the sub-assemblies are pivoted towards each other to define the aperture for receipt of the motor rotor assembly.

3. The motor stator assembly of claim 2, further comprising a locking , mechanism for releasably connecting two of the sub-assemblies to retain the motor stator assembly in its closed configuration.

4. The motor stator assembly of claim 3, wherein the locking mechanism comprises pins of one of the two releasably connected sub-assemblies, and capture channels defined in the other of the two releasably connected sub-assemblies, the pins arranged to slide into the capture channels to lock the two releasably connected sub-assemblies together.

5. The motor stator assembly of claim 1, wherein the motor stator is substantially annular in shape, the motor stator thereby defining a ring-like portion and a conduit, and wherein the assembly includes a plurality of sub-assemblies, each sub-assembly forming an azimuthal portion of the assembly and comprising an azimuthal portion of the motor stator.

6. The motor stator assembly of claim 5, wherein the stator windings are non-overlapping.

7. The motor stator assembly of claim 1, wherein the motor stator housing is substantially cylindrical in shape and has an inwardly-facing flange.

8. The motor stator assembly of claim 7, wherein the motor rotor assembly has a groove arranged to receive the flange of the motor stator housing to axially retain the rotor assembly within the stator assembly.

9. The motor stator assembly of claim 8, further comprising an impeller mechanism coupled to the motor rotor assembly, and a seal mounted between the motor rotor assembly and the impeller mechanism.

10. The motor stator assembly of claim 1 comprising three said subassemblies.

11. The motor stator assembly of claim 10, wherein each of the respective stator windings of the three sub-assemblies corresponds to a separate phase of a three-phase motor circuit.

12. The motor stator assembly of claim 1, wherein the respective stator windings of the sub-assemblies are electrically interconnected by flexible cable interconnectors extending between the sub-assemblies.

13. A motor stator assembly for use in a blood pump, the motor stator assembly defining a central aperture configured to receive a motor rotor assembly, the motor stator assembly comprising:

a motor stator having multiple stator windings; and a housing;

the stator and housing together forming a plurality of sub-assemblies, wherein each sub-assembly includes a respective stator winding and forms an azimuthal portion of the motor stator assembly and wherein the sub-assemblies are mechanically joined by, and pivotable about, at least one hinge member, to define an open configuration in which the sub-assemblies are pivoted away from each other, and a closed configuration in which the sub-assemblies are pivoted towards each other to define the aperture for receipt of the motor rotor assembly.

14. The motor stator assembly of claim 15, wherein the stator windings are non-overlapping.

15. The motor stator assembly of claim 13, wherein the stator windings are electrically interconnected by flexible cable interconnectors extending between the sub-assemblies.

16. The motor stator assembly of claim 13, wherein the housing comprises a biocompatible material.

17. A blood pump comprising:

a motor stator assembly which is substantially annular in shape and defines a central aperture therein, and wherein the motor stator assembly includes multiple stator windings; the motor stator assembly comprising a plurality of sub-assemblies having a respective stator winding, wherein each sub-assembly forms an azimuthal portion of the motor stator assembly, the sub-assemblies being mechanically joined by, and pivotable about, at least one hinge member, to define an open configuration with the sub-assemblies pivoted away from each other, and a closed configuration with the sub-assemblies pivoted towards each other to define the aperture; and a motor rotor assembly positioned within the aperture of the motor stator assembly to form an electric motor therewith for pumping blood.

18. A blood pump according to claim 17, wherein the motor rotor assembly comprises:

an impeller; and a motor rotor mechanically connected to the impeller, motor rotor constructed and arranged to be electromagnetically actuated by the motor stator assembly.

19. A pump for pumping a flow of blood therethrough, the pump having an electric motor comprising a cylindrical stator assembly and a rotatable rotor assembly disposed within the stator assembly, the stator assembly having multiple, non-overlapping windings disposed within corresponding azimuthal sections of the stator assembly;

the azimuthal sections of the stator assembly being mechanically connected along at least one axially directed pivot, and by a manually operable locking mechanism between any adjacent two of the azimuthal sections, to form a cylindrical structure defining a central aperture within which the rotor is adapted to rotate in response to electrical activity in the stator windings;

the azimuthal sections of the stator assembly being mechanically separable, by manually releasing the locking assembly, for removal and installation of the rotor assembly.

20. The pump of claim 19 comprising three azimuthal sections and corresponding stator windings.

21. The pump of claim 19, wherein the azimuthal sections are interconnected at one end of the cylindrical structure by flexible cables, the pump having a centrifugal impeller attached to the rotor and disposed at the other end of the cylindrical structure.

22. The pump of claim 21, wherein individual leads and returns from the stator windings are routed through the flexible cables.

23. The pump of claim 19, wherein the locking mechanism comprises pins of one of the two adjacent azimuthal sections, and capture channels defined in the other of the two adjacent azimuthal sections, the pins arranged to slide into the capture channels to lock the two adjacent azimuthal sections together to form the cylindrical structure.

24. The pump of claim 19, wherein the locking mechanism further comprises a spring arranged to bias the pins toward the capture channels.

25. The pump of claim 19, wherein the locking pins are longitudinally spaced along the stator assembly, with each pin attached to an associated, exposed tab; the tabs arranged to be forced together to withdraw the pins from the capture channels.

26. The pump of claim 19 constructed for axial flow, wherein the rotor a assembly is disposed completely within a blood flow conduit extending through the stator assembly.

27. An articulating motor stator assembly, comprising multiple azimuthal sections positionable in parallel to form a cylindrical structure with each azimuthal section extending the length of the structure; the sections mechanically coupled by at least one hinge pivotable about an axis extending along the length of the cylindrical structure; the sections each containing a respective electrical winding for receiving electrical current to drive a motor rotor assembly positioned within the cylindrical structure; the stator assembly further comprising a manually operable locking mechanism releasably connecting two adjacent azimuthal sections and adapted to be released to enable articulation of the stator assembly for insertion and removal of the rotor assembly.

28. The articulating motor stator assembly of claim 27, wherein the azimuthal sections are electrically interconnected by flexible cables extending directly between adjacent sections.

* * * * *

UNITED STATES PATENT AND TRADEMARK OFFICE
CERTIFICATE OF CORRECTION

PATENT NO.    : 6,018,208
DATED         : January 25, 2000
INVENTOR(S)   : Timothy R. Maher, Douglas C. Thomas, and Thomas C. Rintoul It is certified that error appears in the above-identified patent and that said Letters Patent is hereby corrected as shown below:

Column 9,
Line 16, between the word locking and mechanism please delete the comma.

Column 10,
Line 36, before the word motor rotor please insert -- the --.
Line 47, before the word adjacent please replace any with an.

Signed and Sealed this

Twenty-fifth Day of September, 2001

Attest:

NICHOLAS P. GODICI
Attesting Officer       Acting Director of the United States Patent and Trademark Office